US007782452B2

(12) United States Patent
Mehanian et al.

(10) Patent No.: US 7,782,452 B2
(45) Date of Patent: Aug. 24, 2010

(54) SYSTEMS AND METHOD FOR SIMULTANEOUSLY INSPECTING A SPECIMEN WITH TWO DISTINCT CHANNELS

(75) Inventors: Courosh Mehanian, Seattle, WA (US); Hans J. Hansen, Pleasanton, CA (US); Yingjian Wang, Fremont, CA (US); Yuval Ben-Dov, Cambridge, MA (US); Zheng-Wu Li, Milpitas, CA (US); Andrew V. Hill, San Jose, CA (US); Mehdi Vaez-Iravani, Los Gatos, CA (US); Kurt Zimmermann, San Jose, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 361 days.

(21) Appl. No.: 11/848,516

(22) Filed: Aug. 31, 2007
(Under 37 CFR 1.47)

(65) Prior Publication Data
US 2009/0059215 A1    Mar. 5, 2009

(51) Int. Cl.
*G01N 21/00* (2006.01)
(52) U.S. Cl. .................................. 356/237.2
(58) Field of Classification Search .... 356/237.1–237.5
See application file for complete search history.

(56) References Cited

U.S. PATENT DOCUMENTS

| | | | |
|---|---|---|---|
| 5,822,055 A | 10/1998 | Tsai et al. | |
| 6,078,386 A | 6/2000 | Tsai et al. | |
| 6,288,780 B1 | 9/2001 | Fairley et al. | |
| 6,654,109 B2 | 11/2003 | Li et al. | |
| 6,673,637 B2 | 1/2004 | Wack et al. | |
| 6,694,284 B1 | 2/2004 | Nikoonahad et al. | |
| 6,806,951 B2 | 10/2004 | Wack et al. | |
| 6,816,249 B2 | 11/2004 | Fairley et al. | |
| 6,818,459 B2 | 11/2004 | Wack et al. | |
| 6,829,559 B2 | 12/2004 | Bultman et al. | |
| 6,856,436 B2 | 2/2005 | Brukilacchio et al. | |
| 6,891,610 B2 | 5/2005 | Nikoonahad et al. | |
| 6,917,419 B2 | 7/2005 | Fielden et al. | |

(Continued)

OTHER PUBLICATIONS

International Search Report & Written Opinion, PCT/US2008/074435, mailed Feb. 4, 2009.

*Primary Examiner*—Michael P Stafira
(74) *Attorney, Agent, or Firm*—Kevin L. Daffer; Daffer McDaniel, LLP

(57) ABSTRACT

A system is provided herein for inspecting a specimen. In one embodiment, the system may include a dual-channel microscope, two illuminators, each coupled for illuminating a different channel of the dual-channel microscope and two detectors, each coupled to a different channel of the dual-channel microscope for acquiring images of the specimen. Means are provided for separating the channels of the dual-channel microscope, so that the two detectors can acquire the images of the specimen at substantially the same time. In one embodiment, the channels of the dual-channel microscope may be spectrally separated by configuring the two illuminators, so that they produce light in two substantially non-overlapping spectral ranges. In another embodiment, the channels of the dual-channel microscope may be spatially separated by positioning the two detectors, so that the illumination light do not overlap and the fields of view of the two detectors do not overlap within a field of view of an objective lens included within the system.

30 Claims, 7 Drawing Sheets

U.S. PATENT DOCUMENTS

| | | |
|---|---|---|
| 6,919,957 B2 | 7/2005 | Nikoonahad et al. |
| 6,922,236 B2 | 7/2005 | Vaez-Iravani et al. |
| 7,049,155 B2 | 5/2006 | Reinhorn |
| 7,049,586 B2 | 5/2006 | Reinhorn |
| 7,153,015 B2 | 12/2006 | Brukilacchio |
| 7,164,475 B2 | 1/2007 | Fairley et al. |
| 7,190,459 B2 | 3/2007 | Reinhorn |
| 7,456,954 B2 * | 11/2008 | Weiss et al. .................. 356/318 |
| 2002/0089741 A1 | 7/2002 | Kuhn |
| 2004/0207836 A1 * | 10/2004 | Chhibber et al. ......... 356/237.4 |
| 2005/0152029 A1 | 7/2005 | Endo |
| 2006/0007434 A1 * | 1/2006 | Furman et al. ........... 356/237.2 |
| 2007/0053200 A1 | 3/2007 | Brukilacchio |
| 2007/0058389 A1 | 3/2007 | Brukilacchio |

* cited by examiner

SYSTEMS AND METHOD FOR SIMULTANEOUSLY INSPECTING A SPECIMEN WITH TWO DISTINCT CHANNELS

BACKGROUND OF THE INVENTION

1. Field of the Invention

This invention relates to inspection systems and, more particularly, to systems and methods for simultaneously inspecting a specimen with two distinct inspection channels.

2. Description of the Related Art

The following descriptions and examples are given as background only.

Fabricating semiconductor devices, such as logic and memory devices, typically includes processing a substrate using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during the fabrication of semiconductor devices to detect defects on wafers, thereby promoting higher yield and higher profits. Inspection has always played an important role in semiconductor fabrication. However, as the dimensions of semiconductor devices decrease, inspection becomes even more important to the successful manufacture of acceptable semiconductor devices. For instance, detecting defects of decreasing size has become increasingly necessary, since even relatively small defects can cause unwanted aberrations in the semiconductor device.

Many different types of inspection tools have been developed for the inspection of semiconductor wafers, including optical and E-beam systems. Most optical inspection systems are characterized as either bright-field (BF) or dark-field (DF) systems. These inspection systems generally differ in the manner in which light is directed to, and collected from, the surface of a specimen. For example, bright-field inspection systems direct light to a specimen at a particular angle (e.g., normal to the surface of the specimen) and measure the amount of light reflected from the surface of the specimen at a similar angle. Dark-field inspection systems, on the other hand, detect the amount of light that is scattered from the surface of a specimen when light is supplied to the specimen, typically at an oblique angle of incidence. The collection optics used in dark-field systems are typically positioned out of the path of the reflected light so that only scattered light is collected.

The type of inspection tool used for inspecting a particular semiconductor wafer is generally chosen based on characteristics of the wafer, as well as characteristics of the defects of interest. For example, BF inspection systems are configured for detecting defects that primarily reflect light, such as pattern defects. In BF inspection systems, high-resolution imaging optics are combined with a small pixel size to provide images with relatively high spatial resolution (e.g., between about 100 nm and 500 nm). This makes BF imaging particularly useful for detecting and classifying defects whose sizes are on the order of the design rule. However, BF inspection systems tend to be slower than DF systems because of their high spatial resolution.

DF inspection systems are configured for detecting defects that primarily scatter light, such as particles. In dark-field inspection systems, relatively flat areas on the specimen scatter very little light back to the detector, resulting in a predominantly dark image. Surface features or objects protruding above the surface of the specimen scatter light toward the detector to produce light areas in an otherwise dark image. Dark-field inspection systems, therefore, produce dark images except where circuit features, particles or other irregularities exist. In some cases, Fourier filtering may be used in a dark-field system to enhance signal to noise ratios by filtering out the repetitive patterns of light produced by circuit features on the specimen.

Dark-field systems typically provide much higher throughput than bright-field systems. For example, dark-field systems provide a larger pixel-to-defect ratio, permitting faster inspections for a given defect size and pixel rate. In one example, the spatial resolution of a dark-field inspection system may range between about 500 nm and about 2.0 μm.

Typically, no one optical inspection system can detect all defects. As noted above, dark-field systems are generally configured for detecting defects that scatter light, while bright-field systems detect defects that reflect light. Although one-dimensional defect detection algorithms can be separately applied to dark-field and bright-field data to detect both types of defects (within the constraints set by noise sources that limit sensitivity), there are some defects which can only be detected in a two-dimensional decision space.

To illustrate this concept, a two-dimensional histogram of bright-field difference vs. dark-field difference 400 is shown in FIG. 7. The main cloud of data points 410 represents normal pixels, or pixels where no defects are present. In some cases, bright-field defects and dark-field defects can be detected using one-dimensional algorithms, if the light collected from the defects exceeds the bright-field and dark-field noise floors 420 and 440, respectively. For example, satellite cloud 430 represents a defect that may be detected with a one-dimensional algorithm operating on a bright-field image. Likewise, satellite cloud 450 represents a defect that may be detected with a one-dimensional algorithm operating on a dark-field image. However, satellite cloud 460 represents a defect that is below the noise floors of the bright-field and dark-field systems, and therefore, cannot be detected with a one-dimensional algorithm operating on either the bright-field image or the dark-field image alone. Instead, satellite cloud 460 can only be detected with a two-dimensional algorithm operating on the combined results of bright-field and dark-field imaging.

Some prior art inspection systems have tried to increase the range of detectable defects by combining bright-field and dark-field imaging. In one prior art system, bright-field imaging is performed on a wafer during a first inspection run. After results of the first run are processed to determine the bright-field defects, the wafer is illuminated with dark-field illumination in a second inspection run to generate a list of dark-field defects. The problem with this system is that throughput, or the time needed to process a single wafer, is poor and it does not have the capability of using the combined results from the bright-field and dark-field images before the results are processed to determine defects. Instead, the defect detection algorithm used in the prior art system sets thresholds above which a feature is considered a defect, and only passes bright-field and dark-field defects which surpass these thresholds. The prior art system is, therefore, unable to detect defects that fall below the thresholds (or noise floors) individually set for the bright-field and dark-field channels.

In an attempt to solve the above-mentioned problems, a few prior art inspection systems have been designed to provide simultaneous bright-field and dark-field illumination to the wafer. These systems use a single light source (usually a monochromatic or narrowband source, such as a laser) to provide bright-field and dark-field illumination to the wafer. Bright-field and dark-field detectors are positioned within the system, so that reflected light is detected by the bright-field detector and scattered light is detected by the dark-field detector. The information from both detectors is supplied to a defect detection algorithm to determine the location of defects on the wafer.

Unfortunately, currently available systems capable of providing simultaneous bright-field and dark-field imaging have their own set of disadvantages. In the prior art system described above, for example, throughput is improved by providing simultaneous bright-field and dark-field inspection. However, inspection is performed by scanning a spot with a relatively large pixel size across the surface of the wafer. Although high throughput is achieved, the large pixel size significantly decreases the resolution of the bright-field image. In addition, the prior art system uses a single light source for both bright-field and dark-field illumination. This limits the flexibility to independently optimize the characteristics of the bright-field and dark-field illumination. Furthermore, the single light source typically comprises a monochromatic or narrowband source, such as a laser. However, narrowband light sources introduce contrast variations and coherent noise into the bright-field image, which further reduces bright-field sensitivity and resolution.

A need remains for an improved wafer inspection system, which provides simultaneous bright-field and dark-field imaging, while overcoming the disadvantages and limitations of currently available systems.

SUMMARY OF THE INVENTION

The following description of various embodiments of inspection systems and methods is not to be construed in any way as limiting the subject matter of the appended claims.

According to one embodiment, a system is provided herein for inspecting a specimen. In general, the system may include a dual-channel microscope, two illuminators, each coupled for illuminating a different channel of the dual-channel microscope, two detectors, each coupled to a different channel of the dual-channel microscope for acquiring images of the specimen, and means for separating the channels of the dual-channel microscope, so that the two detectors can acquire the images of the specimen at substantially the same time. Although not limited to inspecting wafers, the system described herein may be alternatively be referred to as a "wafer inspection system."

In one embodiment, at least one of the illuminators may include a broadband illumination source, such as a light emitting diode (LED) source. In some cases, the LED source may include an array of light emitting diodes, each having a coating that enables the diode to produce white light. In other cases, the LED source may include two or more different colors of light emitting diodes, each configured to produce light in a substantially different spectral range.

In one embodiment, said means includes spectrally separating the channels of the dual-channel microscope by configuring the two illuminators, so that they produce light in two substantially non-overlapping spectral ranges. In some cases, the two illuminators may each be coupled for providing bright-field illumination to the dual-channel microscope. In other cases, the two illuminators may each be coupled for providing dark-field illumination to the dual-channel microscope. In yet other cases, the two illuminators may be separately coupled for providing bright-field illumination and dark-field illumination to the dual-channel microscope.

In another embodiment, said means includes spatially separating the channels of the dual-channel microscope. For example, the system may include an objective lens, which is coupled for receiving light propagating from the specimen in response to illumination provided to the specimen by the two illuminators. The objective lens has a field of view (FOV) over which the lens can collect light propagating from the specimen. The two detectors also have a respective field of view over which the detector can receive a portion of the light propagating from the specimen. To achieve spatial separation between the channels, the two illuminators direct light to two different, non-overlapping regions of the field of view of the objective lens. In addition, the two detectors are positioned so that the fields of view of the two detectors do not overlap within the field of view of the objective lens. In some cases, cross-talk between the two channels may be reduced by positioning the two illuminators, so that illumination from one of the illuminators crosses over an illumination path of the other illuminator. The two illuminators may provide bright-field illumination, dark-field illumination or any combination thereof to the specimen.

Another system for inspecting a specimen is provided herein according to another embodiment. The system may generally include a pair of illumination subsystems, an objective lens and a pair of detection subsystems. The pair of illumination subsystems may be coupled for directing a first beam of light and a second beam of light to the specimen at substantially the same time. The objective lens may be coupled for receiving light propagating from the specimen in response to the first and second beams of light. Finally, the pair of detection subsystems may each be coupled for generating output signals in response to a respective portion of the light propagating from the specimen. As one advantage, the output signals may be generated at substantially the same time.

The pair of illumination subsystems may be configured somewhat differently in various embodiments of the invention. In one embodiment, for example, the pair of illumination subsystems may each include a bright-field illuminator. In another embodiment, the pair of illumination subsystems each include a dark-field illuminator. In yet another embodiment, the pair of illumination subsystems includes one bright-field illuminator and one dark-field illuminator. Regardless of the particular illumination scheme chosen, at least one of the illumination subsystems may include a light emitting diode (LED) source, as mentioned above. In one example, the LED source may include an array of light emitting diodes, each having a coating that enables the diode to produce white light. In another example, the LED source may include an array of light emitting diodes including at least three different colored LEDs. In some cases, the LED source can be configured to produce white light by supplying approximately the same amount of current to each LED in the array. In other cases, the LED source can be customized to produce light in a substantially different spectral range by varying the amount of current supplied to one or more LEDs in the array.

Each detection subsystem has a field of view, which is positioned within a field of view of the objective lens for detecting the light propagating from the specimen. The system also includes separation means configured to prevent light propagating from the specimen in response to the first beam of light from interfering with light propagating from the specimen in response to the second beam of light. In one embodiment, the separation means are provided by configuring the pair of illumination subsystems, such that each generates light in a substantially different, non-overlapping spectral range. In another embodiment, the separation means are provided by arranging the pair of illumination subsystems and the pair of detection subsystems, such that the regions of illumination and the fields of view of the detection subsystems are spatially separated from one another.

According to another embodiment, a method is provided herein for inspecting a specimen with simultaneous bright-field and dark-field illumination. In general, the method may include generating bright-field illumination with one light source and dark-field illumination with another light source. The step of generating may include using a light emitting diode (LED) source to generate the bright-field illumination, the dark-field illumination or both. Next, the method may supply the bright-field illumination and the dark-field illumination to the specimen at substantially the same time. Light reflected from the specimen in response to the bright-field illumination, as well as light scattered from the specimen in response to the dark-field illumination, may then be detected at substantially the same time.

Another system for inspecting a specimen is provided herein in accordance with yet another embodiment of the invention. Unlike the previous embodiments, the inspection system described herein may include at least one illumination subsystem coupled for directing light to the specimen and at least one detection subsystem coupled for generating output signals in response to light propagating from the specimen. The output signals may be used to detect defects on the specimen.

The at least one illumination subsystem preferably includes a light emitting diode (LED) source. In some cases, the LED source may include an array of light emitting diodes, each having a coating that enables the diode to produce white light. In other cases, the LED source may comprise an array of light emitting diodes including at least two different colors of LEDs. In this case, the LED source may be configured to produce white light (by supplying approximately the same amount of current to each LED in the array) or light in a substantially different spectral range (by varying the amount of current supplied to one or more LEDs in the array).

BRIEF DESCRIPTION OF THE DRAWINGS

Other objects and advantages of the invention will become apparent upon reading the following detailed description and upon reference to the accompanying drawings in which.

Figure 1:
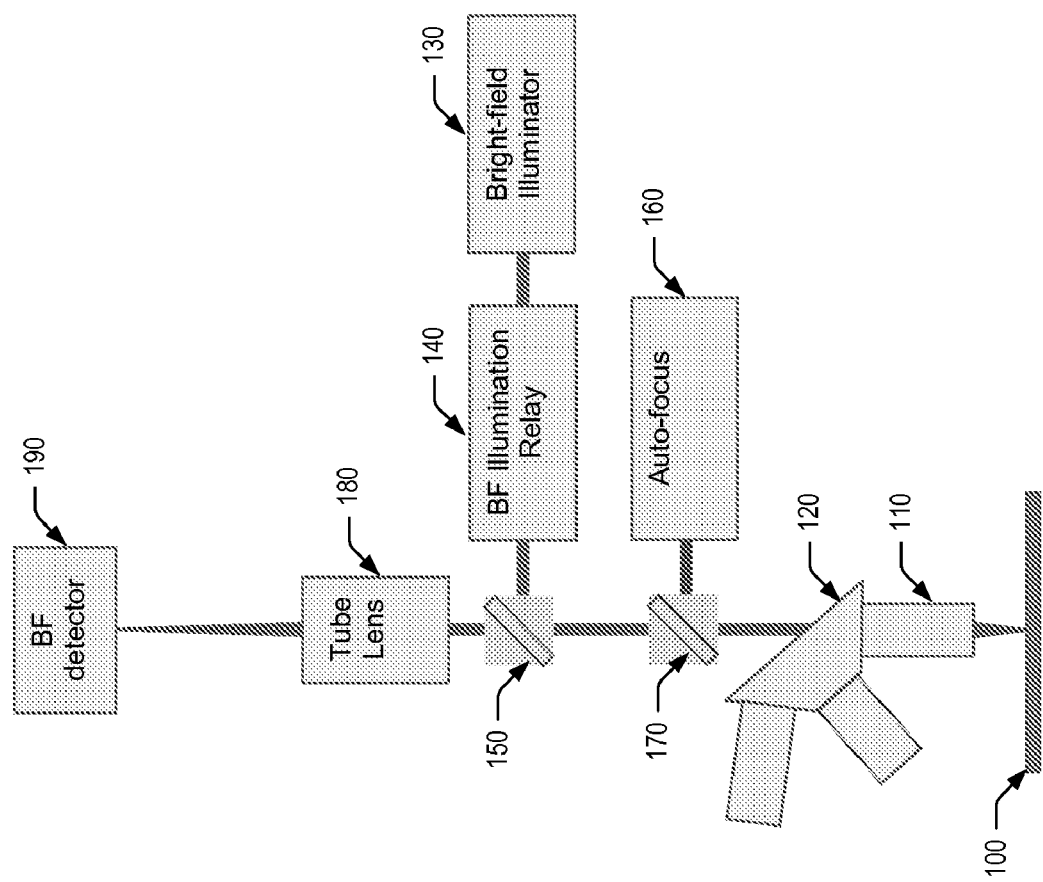
FIG. 1 is a block diagram illustrating one embodiment of a system configured to inspect a specimen with a single bright-field channel.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

As used herein, the term "specimen" refers to a reticle or a wafer. The terms "reticle" and "mask" are used interchangeably herein. A reticle generally includes a transparent substrate such as glass, borosilicate glass, and fused silica having opaque regions formed thereon in a pattern. The opaque regions may be replaced by regions etched into the transparent substrate. Many different types of reticles are known in the art, and the term reticle as used herein is intended to encompass all types of reticles.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, a conductive material, and a semiconductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features or periodic structures. Formation and processing of such layers of material may ultimately result in completed devices. Many different types of devices may be formed on a wafer, and the term wafer as used herein is intended to encompass a wafer on which any type of device known in the art is being fabricated.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

There are many wafer inspection systems available on the market today. In one respect, the wafer inspection systems may be classified according to the amount of spatial resolution they are capable of providing, which correlates well with achievable sensitivity. Of course, sensitivity usually scales inversely with throughput. For example, the most sensitive systems, and thus the slowest, are scanning electron microscope (SEM) inspection systems. These systems are generally capable of distinguishing features and defects within a range of about 20 nm to about 100 nm. Just above SEM systems are optical systems usually termed "micro inspection systems." These systems achieve spatial resolutions between about 100 nm and about 500 nm, and are usually operated in bright-field imaging mode. Just above this are optical systems that provide a spatial resolution between about 0.5 µm and about 2.0 µm. These systems usually have a dark-field architecture and can be imaging or spot scanning systems. They typically achieve the best sensitivity to particles at a given throughput. Finally, optical systems with spatial resolutions of about 2.0 µm and above are termed "macro inspection systems." These systems are used when throughputs of 100 wafers per hour (wph) or more are required (wafer throughput refers to number of 300 mm wafers inspected per hour).

FIG. 1 illustrates one embodiment of a macro inspection system. In general, the macro inspection system shown in FIG. 1 includes an illumination subsystem for providing illumination to a wafer 100, a single-channel microscope for collecting light reflected from a surface of the wafer, and a detection subsystem for generating images of the wafer based on the reflected light.

In some cases, the wafer 100 may be supported by an xyzφ stage (not shown). The stage may be used to align the wafer, and in some cases, to move the wafer in a serpentine path so that the surface of the wafer may be scanned with an objective field of view (FOV). The width of an individual segment of the serpentine path (equal to the FOV) is called the swath width (or height). Although there is a concomitant loss of throughput associated with the serpentine motion compared to a single linear motion, the trade-off is reasonable for systems with a relatively large swath width and throughputs in the range of 100 wph are achievable.

The macro inspection system shown in FIG. 1 is configured to operate in bright-field mode. For example, light from bright-field illuminator 130 is introduced into an objective lens 110 via a beamsplitter 150. Light emitted by the bright-field illuminator is imaged onto the pupil of the objective lens by an illumination relay lens 140. In some cases, an auto-focus unit 160 may introduce its own beam of light into the objective via a dichroic beamsplitter 170. The auto-focus beam monitors changes in wafer height relative to the objective lens and enables the system to stay in focus via a feedback loop. However, the wavelength of the auto-focus beam should be outside the spectral range of the bright-field illuminator to minimize cross-talk between the auto-focus channel and the bright-field channel. In one example, the auto-focus wavelength may be centered at about 680 nm when bright-field illuminator 130 is configured for generating light in the spectral range of about 420 nm to about 650 nm. To avoid blocking the collection channel, dichroic beamsplitter 170 only reflects light with wavelengths above a certain threshold (e.g., 665 nm). All wavelengths below the threshold are transmitted through the dichroic beamsplitter.

In some cases, the objective lens 110 may be mounted on a turret 120, as shown in FIG. 1. The turret can be used to select a desired objective, and hence, a desired optical magnification of the image of the wafer. As the light reflects off the surface of the wafer, the objective lens collects the reflected light and produces an image of the wafer at infinity. The collected light is converged into a real image by tube lens 180. The image is detected by a sensor 190 (e.g., a CCD camera) and conveyed to a computer (not shown) for further processing.

In one respect, the macro inspection system shown in FIG. 1 improves upon conventional inspection systems by using a broadband source 130 to provide the bright-field illumination. Tungsten filaments and plasma arc lamps are two examples of commonly used broadband bright-field illuminators. The broadband source provides the advantage of suppressing noise that originates from wafer variation, a serious limitation for inspection systems that rely purely on narrow-band sources.

Unfortunately, the macro inspection system shown in FIG. 1 provides only bright-field illumination, and therefore, cannot be used to detect defects which can only be detected in dark-field images or the combined results of bright-field/dark-field imaging. Another limitation of the macro inspection system described above is the illuminator chosen to provide broadband illumination. As noted above, most macro inspection systems use tungsten filaments or plasma arc lamps to provide broadband illumination. However, these sources generate light within a predefined spectral range, which cannot be tailored to the application. If an alternative spectral range is desired, the source must be replaced with an alternative source configured for that range. Furthermore, conventional sources have limited lifetimes, which require the sources to be replaced frequently. Arc lamps, for example, need to be replaced every 1,000 to 3,000 hours of operation. This is both costly and time consuming. For instance, wafer inspection systems are critical to the operation of a modern semiconductor fabrication facility. Frequent replacement of the illumination system can mean a great deal of lost inspection time, which translates to lost production time and increased production costs for the facility.

Improved wafer inspection systems are shown in FIGS. 2, 3, 5, and 6 and described in more detail below. The improved wafer inspection systems provide many advantages over conventional inspection systems and the system shown in FIG. 1. For example, many of the wafer inspection systems described below provide simultaneous bright-field and dark-field inspection by collecting both reflected and scattered light from the specimen at substantially the same time. A dual-channel microscope with separate bright-field and dark-field channels is used for this purpose. In some cases, the data from the bright-field and dark-field channels may be combined prior to defect detection. This ensures sensitivity to a wide range of defects, including those that can only be detected in a bright-field difference vs. dark-field difference decision space. For example, the present system may be able to detect a wide range of defect types including, but not limited to, particles, films, residues, stains, pits, bumps and scratches.

Unlike other inspection systems, the wafer inspection systems described below use separate illumination subsystems to illuminate the bright-field and dark-field channels. This enables the systems to separately optimize the bright-field and dark-field illumination spectra, enabling each to be tailored for a different application.

At least one of the illumination subsystems includes a broadband light source. In one embodiment, the broadband light source uses an array of light emitting diodes (LEDs) to generate visible or white light. In some cases, white light may be generated by combining the light generated by differently colored LEDs. For example, red, green and blue LEDs may be combined and driven at maximum current to produce illumination, which is more or less white. In some cases, white light may be generated by using more than three different colors in the LED array. In other cases, single color LEDs may be capped with an optical element coated with phosphor to produce white light. A combination of multi-colored LEDs and phosphor coated LEDs may also be used to generate white light. The array of LEDs may be placed in any configuration necessary to provide the desired spectrum of illumination.

LEDs provide many advantages over conventional broadband light sources. First of all, LEDs have significantly longer lifetimes than conventional arc lamps. For instance, an LED source may provide approximately 20,000 to 100,000 hours of operation, depending on how hard the source is driven. The longer LED lifetime significantly reduces the production down time and costs associated with conventional arc lamps, which only provide about 1,000 to 3,000 hours of operation. As another advantage, the LED source provides an illumination spectrum that can be tailored to the defect(s) of interest. For example, defects often respond differently to different colors of light. In some cases, modeling may be used to predict the response a defect may have to a particular color of light. In other cases, the response may be determined empirically. Once a desired response is determined, the illumination spectrum provided by the LED source may be customized by varying the electrical current supplied to one or more colors in the LED array. For example, if the defect(s) of interest are most prominent in blue light, the current supplied to the red and green LEDs may be shut off, while the current to the blue LEDs is maintained. The ability to customize the illumination spectrum enables the systems to provide maximum sensitivity to the defect(s) of interest.

Heretofore, LEDs have not been employed in wafer inspection systems because of their limited brightness. LED technology, however, has advanced tremendously in the past few years, producing LED sources of ever-increasing brightness. This technological advance has prompted the present inventors to utilize LED illumination in the wafer inspection systems described herein, thereby reaping the advantages offered by LED illumination (e.g., long lifetimes and customizable illumination spectra).

Various embodiments of the improved wafer inspection system are illustrated in FIGS. 2, 3, 5 and 6. All illustrated embodiments include at least two illuminators, each of which is coupled for illuminating a different channel of a dual-channel microscope. As mentioned above, at least one of the illuminators includes a broadband source, and more specifically, an LED array configured to provide a desired spectral range. All embodiments also include at least two detectors, each of which is coupled to a different channel of the dual-channel microscope for acquiring images of a specimen under inspection. As described in more detail below, means are provided for separating the channels of the dual-channel microscope, so that the detectors can acquire the images of the specimen at substantially the same time. Although described in the context of macro inspection systems, one skilled in the art would understand how the systems described herein could be modified to provide substantially any spatial resolution deemed appropriate.

Figure 2:
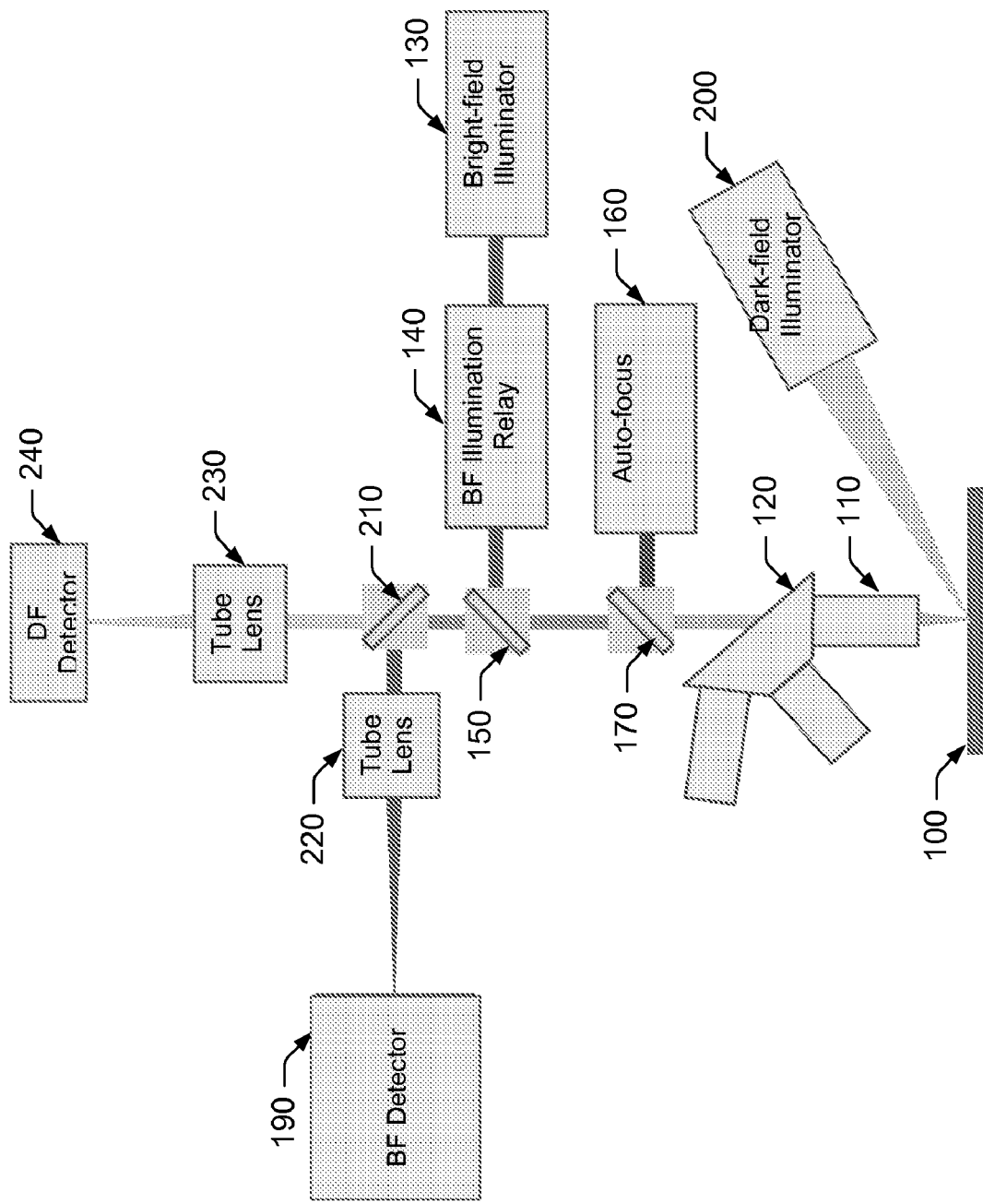
FIG. 2 is a block diagram illustrating one embodiment of a system configured to inspect a specimen with bright-field and dark-field channels.

One embodiment of the improved wafer inspection system is shown in FIG. 2. The embodiment shown in FIG. 2 includes many of the components shown in FIG. 1. For example, the wafer inspection system shown in FIG. 2 includes a stage (not shown) for mounting and aligning a wafer 100 to be inspected within an optical path of the system. An objective lens 110 is included for focusing light onto, and for collecting light from, the surface of the wafer. As noted above, the objective lens 110 may be mounted on a turret 120 to enable the system to select a desired objective, and hence, a desired optical magnification.

Bright-field illuminator 130 generates light, which is directed to the surface of the wafer by illumination relay optics 140, beam splitter 150 and objective lens 110. In one embodiment, the bright-field light illuminates an area of the wafer that corresponds to the field of view of the bright-field detector. In some cases, an additional beam of light from auto-focus unit 160 may be directed to the wafer surface by dichroic beamsplitter 170 and objective lens 110. As the light reflects off the surface of the wafer, the objective lens collects the reflected light and produces an image of the wafer at infinity. The collected light is converged into a real image by a tube lens (e.g., 180 or 220) and detected by a sensor 190 (e.g., a CCD camera). Output signals from the sensor are conveyed to a computer (not shown) for further processing.

The wafer inspection shown in FIG. 2 also includes many components, which were not originally included in the embodiment of FIG. 1. For example, the wafer inspection system shown in FIG. 2 includes an additional illumination subsystem, collection channel and detection subsystem. In one embodiment, a dark-field illuminator 200 is added for illuminating a dark-field channel of the inspection system. As shown in FIG. 2, the dark-field illuminator supplies light to the surface of the wafer from outside of the objective (i.e., not through the objective as in the case of bright-field illumination). The dark-field light may be supplied to the wafer surface at any appropriate angle. In one embodiment, the dark-field field of view (FOV) may overlap at least a portion of the bright-field FOV.

The bright-field and dark-field channels are separated in the embodiment of FIG. 2 by using a different spectral range for each channel. In one embodiment, the bright-field and dark-field illuminators may comprise LED sources having substantially different spectral range. For example, the bright-field channel may be illuminated with predominantly blue LED light, while the dark-field channel is illuminated with predominantly amber light. However, the bright-field and dark-field channels are not limited to any specific spectrum of light, and instead, may be tailored to the bright-field and dark-field defect(s) of interest. In addition, the bright-field and dark-field illuminators may not each include an LED source in all embodiments of the invention. As one alternative, for example, the dark-field illumination may be provided by a laser source. The only requirement in the present embodiment is that the spectra chosen for the bright-field and dark-field channels do not overlap each other, or if they do, that the overlap be filtered out to avoid cross-talk between channels.

Objective lens 110 collects the dark-field light scattered from the surface of the wafer, along with the bright-field light reflected from the wafer surface. Dichroic beamsplitter 210 is included to split the collected light into the appropriate detection channel. In one embodiment, dichroic beamsplitter 210 may be designed to reflect light with wavelengths below, and transmit light with wavelengths above a particular splitting wavelength. As used herein, the term "splitting wavelength" refers to the wavelength between the bright-field and dark-field illumination spectra at which spectral overlap is minimized. Splitting the collected light at this wavelength allows the dichroic beamsplitter to direct reflected light to the bright-field detection channel and scattered light to the dark-field detection channel.

As shown in FIG. 2, each detection channel may include a separate tube lens 220/230 and a separate detector 190/240. The tube lenses are used to converge the reflected and scattered light into real images, which are separately and simultaneously detected by the detectors. The detectors may include any suitable sensor known in the art, examples of which include, but are not limited to, CCD and TDI sensors. As described in more detail below, output signals from the detectors may be conveyed to a computer (not shown) for further processing.

Spectrally separating the two channels enables the detectors to acquire both bright-field and dark-field images of the wafer at substantially the same time. This improves throughput (over systems capable of providing only one mode at a time) and increases sensitivity to a wider range of defects by enabling the detector output signals to be combined before the defects are detected. In addition to bright-field and darkfield defects, for example, the combined results may be processed to locate defects that can only be detected in the bright-field difference vs. dark-field difference decision space.

One embodiment of a spectral separation method has now been described in reference to FIG. 2. However, the spectral separation method is not limited to the exemplary embodiment shown herein. Many alternative embodiments of the method may exist. In one alternative embodiment, for example, both channels of the dual-channel microscope may share a single tube lens (e.g., similar to tube lens 180 of FIG. 1) and spectral separation may be performed after the image convergence by arranging the dichroic beamsplitter 210 after the common tube lens. In another alternative embodiment, the dark-field illuminator 200 may be eliminated and replaced with an additional bright-field illuminator (not shown). This can be achieved, for example, by expanding the LED array of bright-field illuminator 130 to include four different LED colors. The dichroic beamsplitter 210 may be configured so that two LED colors lie on one side of the splitting wavelength and the other two LED colors lie on the other side of the splitting wavelength. Conversely, the bright-field illuminator 130 may be eliminated and replaced with an additional darkfield illuminator (not shown). The additional dark-field illuminator may be positioned for supplying light to the wafer surface at any appropriate angle.

Regardless of the type of illumination used, the two channels may be separated by selecting a different spectral range for each illumination subsystem. In the example provided above, the channels are separated by selecting two substantially different colors or spectra of illumination (e.g., blue and amber light). A dichroic beamsplitter 210 is included to divide the reflected light and the scattered light into the appropriate detection channels. However, it may also be possible for one channel to occupy a portion of the spectrum in between two lobes of the spectral range chosen for the other channel. In some cases, a coating applied to dichroic beamsplitter 210 may be designed to separate the intermediate lobe results from the side lobe results.

Although the spectral separation method described above provides many advantages, it has limited flexibility when it comes to choosing illumination spectra. In some cases, the spectral separation method may prevent at least one of the channels from being tailored to a particular defect of interest. This may limit the maximum achievable sensitivity of the inspection system, and thus, may be undesirable in some embodiments.

Figure 3:
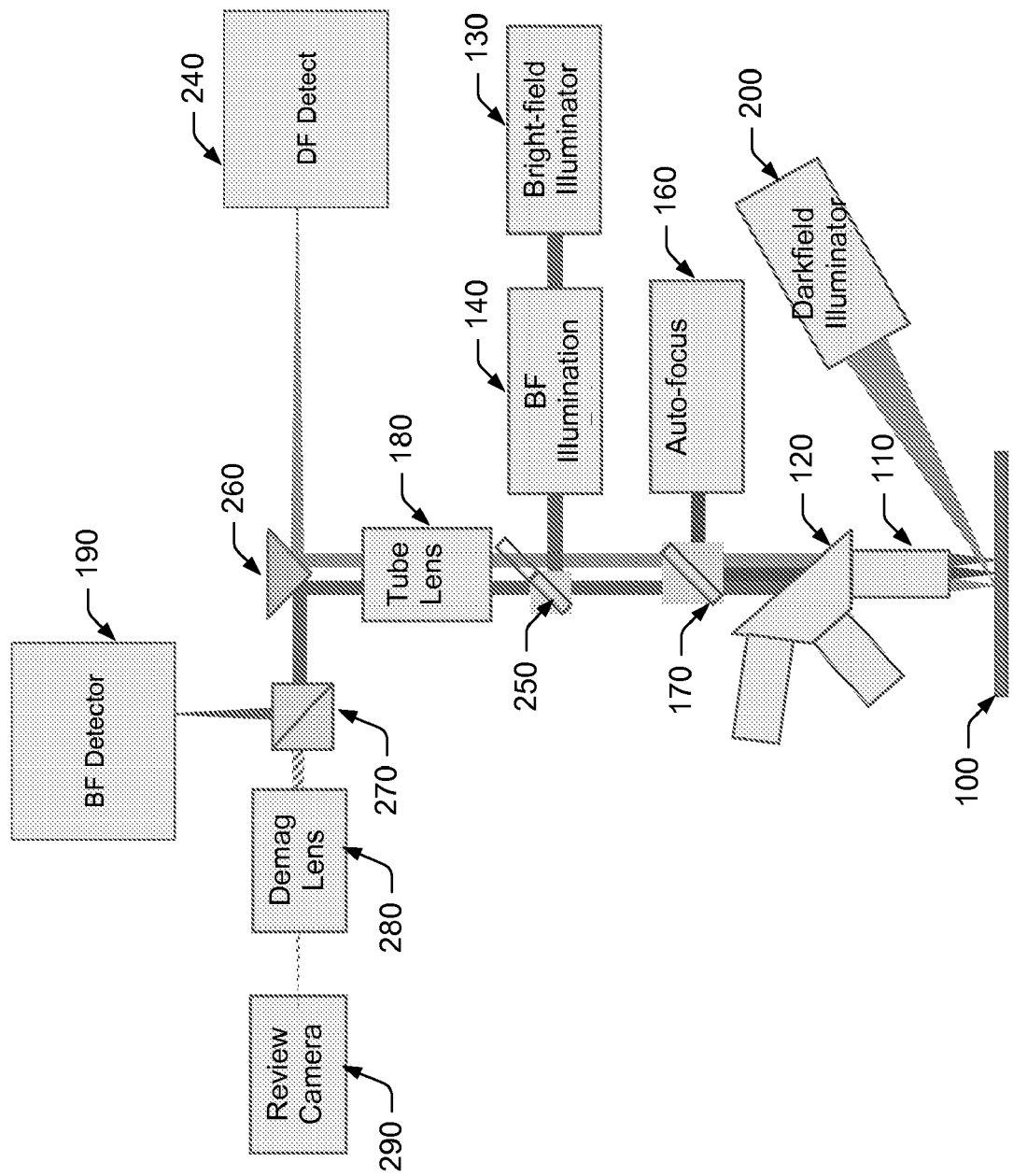
FIG. 3 is a block diagram illustrating another embodiment of a system configured to inspect a specimen with bright-field and dark-field channels.

FIG. 3 illustrates another embodiment of the wafer inspection system in which the two channels of the dual-channel microscope are separated spatially, instead of spectrally. This embodiment may be preferred, for example, when maximum flexibility over the illumination spectra is desired. The spatial separation method is described below in reference to the embodiment shown in FIG. 3. Modifications to the spatial separation method will be described later in this document.

The wafer inspection system shown in FIG. 3 includes many of the same components shown in FIG. 2. For instance, the wafer inspection system includes wafer 100, objective lens 110, turret 120, bright-field illuminator 130, illumination relay optics 140, auto-focus unit 160, beamsplitter 170, tube lens 180 and dark-field illuminator 200. These components generally operate in the manner described above with one exception—the bright-field and dark-field channels are spatially separated and are not required to be spectrally distinct (although they can be). In order to achieve spatial separation, the fields of view of the detectors 190 and 240 must fit within the field of view of objective lens 110 without overlap. The use of linescan CCD or TDI CCD sensors facilitates this goal, because these sensors have footprints that are long and thin. However, the bright-field and dark-field detectors are not limited to linescan CCD or TDI CCD sensors and may be alternatively implemented with any other suitable sensor.

Figure 4B:
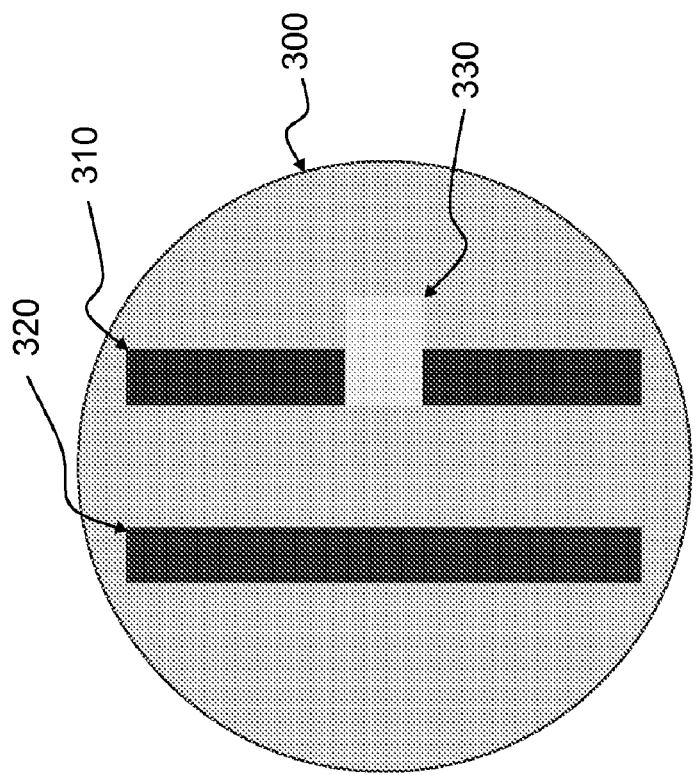
FIG. 4B is a top view illustrating one manner in which the FOV of a review camera may be placed within the FOV of the objective lens.
Figure 4A:
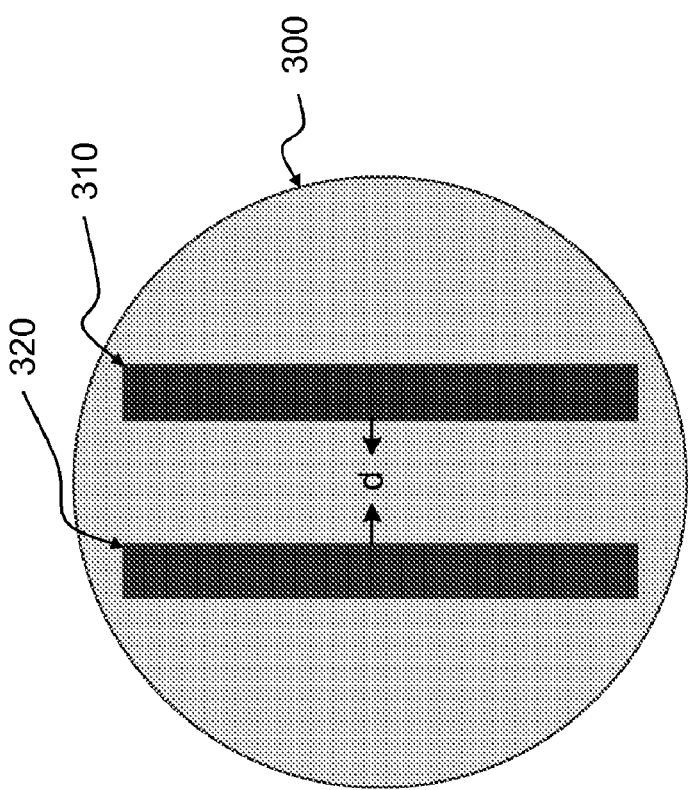
FIG. 4A is a top view illustrating one manner in which the field of views (FOVs) of two detectors may be spatially separated within a FOV of an objective lens.

FIG. 4A illustrates one manner in which the bright-field detector FOV 310 and the dark-field detector FOV 320 may be spatially separated within the FOV 300 of the objective lens 110. In general, FOVs 310 and 320 may be separated by a distance (d), which prevents the FOVs 310 and 320 from overlapping within the FOV 300 of the objective lens. However, the placement of FOVs 310 and 320 is not limited to the particular arrangement shown in FIG. 4A and may be modified, as long as the FOVs 310 and 320 do not come in contact with each other. During inspection, the FOV of the objective lens may be scanned across the wafer to acquire bright-field and dark-field images the wafer surface. In some cases, the wafer may be scanned in a serpentine pattern, as mentioned above.

To accommodate the off-center position of the bright-field FOV 310, the bright-field illumination is introduced at an angle to the optical axis of the objective. The bright-field illumination beamsplitter 250 covers only the corresponding portion of the angular space behind the objective. Dark-field illumination from illuminator 200 is supplied to the wafer surface outside of the objective onto the dark-field FOV 320. In one embodiment, the dark-field illumination crosses over the path of the bright-field illumination to reduce cross-talk between the bright-field and dark-field channels. As described above, objective lens 110 collects the light reflected and scattered from the surface of the wafer and generates bright-field and dark-field images of the wafer at infinity. To avoid blocking the dark-field channel, half of beamsplitter 250 (i.e. the portion covering the dark-field FOV) may comprise a transmissive material.

The reflected light and the scattered light collected by objective lens 110 are converged into real images by tube lens 180. In one embodiment, the bright-field and dark-field images may be separated into the appropriate detection channels by a double-sided mirror 260 in the shape of a prism. However, there are many other suitable optical components that could be used to separate the bright-field and dark-field images. The disclosure set forth herein is considered to cover all such modifications.

In one embodiment, the dark-field image is focused directly onto the dark-field detector 240. On the bright-field side, a majority of the bright-field light is focused onto the bright-field detector 190. However, a small portion of the bright-field light may be split off by a cube beamsplitter 270 and directed to a review camera 290. Review camera 290 may be used to acquire color images of the specimen under inspection. In some cases, an additional optical element 280 may be placed between beamsplitter 270 and review camera 290 to adjust the image magnification in accordance with the imaging requirements.

FIG. 4B illustrates one manner in which the review camera FOV 330 may be arranged within the FOV 300 of the objective lens. As shown in FIG. 4B, the review camera FOV 330 may occupy a portion of the bright-field FOV 310. In this case, the field stop of the bright-field illuminator 130 may include a notch to accommodate the review camera FOV. This allows the review camera to share the illumination and optics of the bright-field channel, thereby reducing costs and complexity.

It is noted, however, that beamsplitter 270, optical element 280, and review camera 290 may not be included in all embodiments of the invention. If eliminated, the bright-field image from double-sided mirror 260 may be focused directly onto the bright-field detector 190. It is also worth noting that beamsplitter 270, optical element 280, and review camera 290 may be added to other embodiments including bright-field inspection, such as those shown in FIGS. 2 and 5.

As described in more detail below, output signals from the bright-field and dark-field detectors may be conveyed to a computer (not shown) for further processing. Because the two channels are separated spatially, the bright-field and dark-field detectors are able to acquire bright-field and dark-field images of the wafer at substantially the same time. This improves throughput (over systems capable of providing only one mode at a time) and increases sensitivity to a wider range of defects by enabling the detector output signals to be combined before defects are determined. In addition to bright-field and dark-field defects, the output signals may be combined to locate defects that can only be detected in the bright-field difference vs. dark-field difference decision space.

One embodiment of a spatial separation method has now been described in reference to FIG. 3. However, the spatial separation method described herein is not limited to the exemplary embodiment shown herein. Many alternative embodiments of the method may exist. In one embodiment, the bright-field and dark-field illuminators may each include LED sources. The LED sources may provide bright-field and dark-field illumination within the same spectral range, or alternatively, within two substantially different spectral ranges. In another embodiment, bright-field illuminator 130 may be implemented with an LED source, while dark-field illuminator 200 is implemented with a narrowband source, such as a laser. This would enable a technician to tailor the illumination to different types of defects and/or regions of the wafer.

Figure 5:
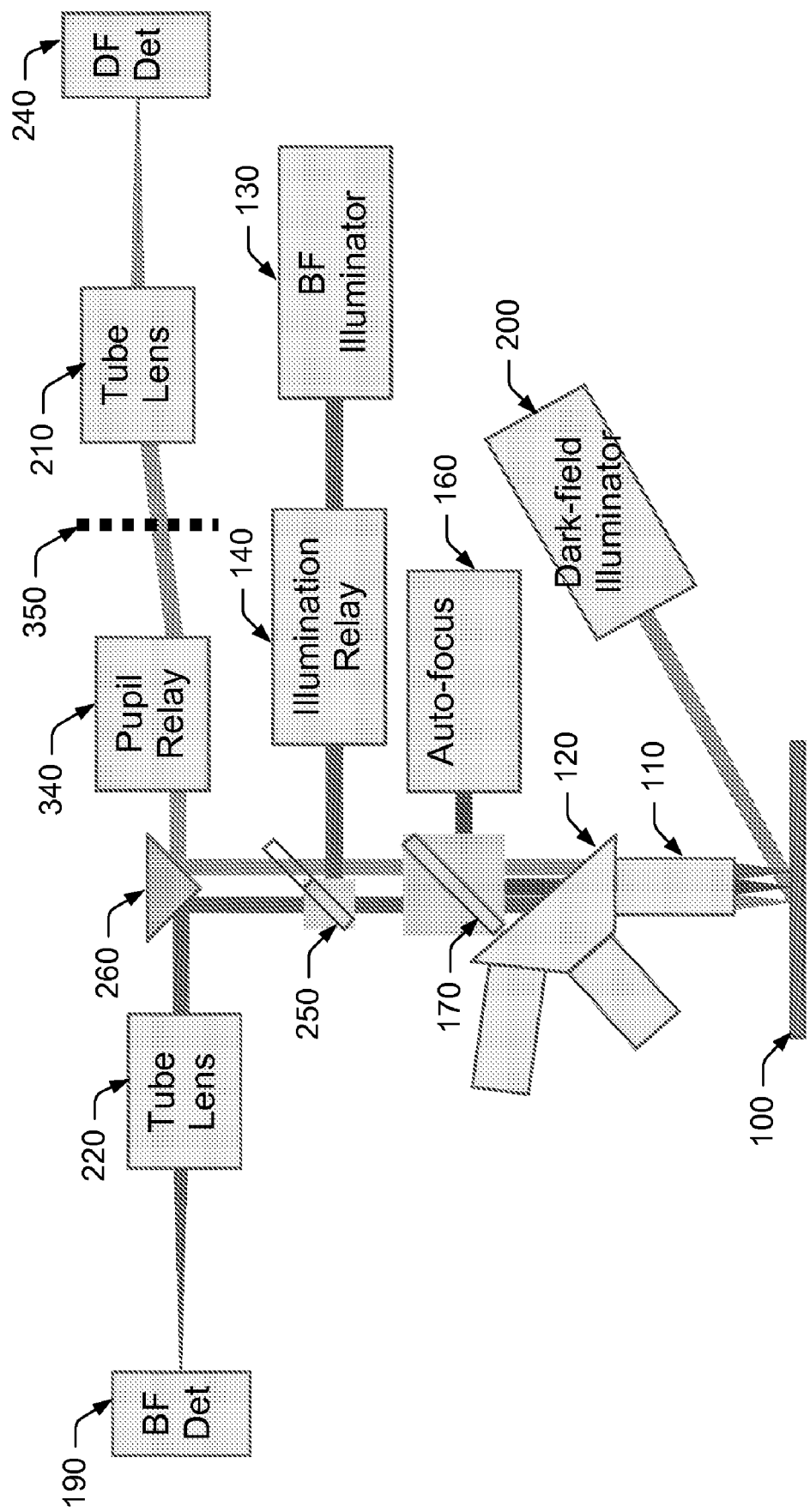
FIG. 5 is a block diagram illustrating yet another embodiment of a system configured to inspect a specimen with bright-field and dark-field channels.

FIG. 5 illustrates an alternative embodiment of the spatial separation method, in which different types of illumination sources are used to inspect different regions of a wafer. Many of the components shown in FIG. 5 are identical to the ones shown in FIGS. 2 and 3. Components having like reference numerals will not be described further herein. The wafer inspection system shown in FIG. 5 differs from the systems of FIGS. 2 and 3 by using a significantly brighter, narrowband source (such as a laser) to provide dark-field illumination to the wafer. The wafer inspection system of FIG. 5 also adds a pupil relay 340 and Fourier filter 350 to the dark-field detection channel between the double-sided mirror 260 and dark-field tube lens 210. The scattered light is reflected to the dark-field channel by prism-shaped mirror 260. Fourier filter 350 is placed at the pupil conjugate to filter out the repeating patterns on the wafer. Fourier filter 350 may be implemented in any manner known in the art. Examples of suitable Fourier filters may include, but are not limited to, chrome masks, liquid crystals, MEMS arrays and other fixed and programmable filter designs.

In some cases, the arrangement shown in FIG. 5 may be used for inspecting memory chips and other semiconductor devices that combine regular repeating arrays with random patterns on the periphery of the arrays. In one embodiment, the dark-field channel may inspect the repeating arrays with high sensitivity, while the bright-field channel inspects the logic and periphery regions of the chip with lesser, albeit adequate sensitivity. The Fourier filter enables the dark-field channel to inspect the repeating arrays with high sensitivity by filtering out the repeating patterns of scattered light produced by the array. Once the repeating patterns are filtered out, the array looks like an unpatterned surface to the dark-field channel, thereby enabling dark-field defects to be detected with high sensitivity.

Although described as such, the spatial separation method is not limited to the separation of bright-field and dark-field channels. Instead, the spatial separation method may be applied to any two channels that carry different kinds of information about the wafer being inspected. In one example, the bright-field illumination subsystem shown in FIG. 5 may be eliminated and replaced with an additional dark-field illuminator, as shown in FIG. 6 and described below.

Figure 6:
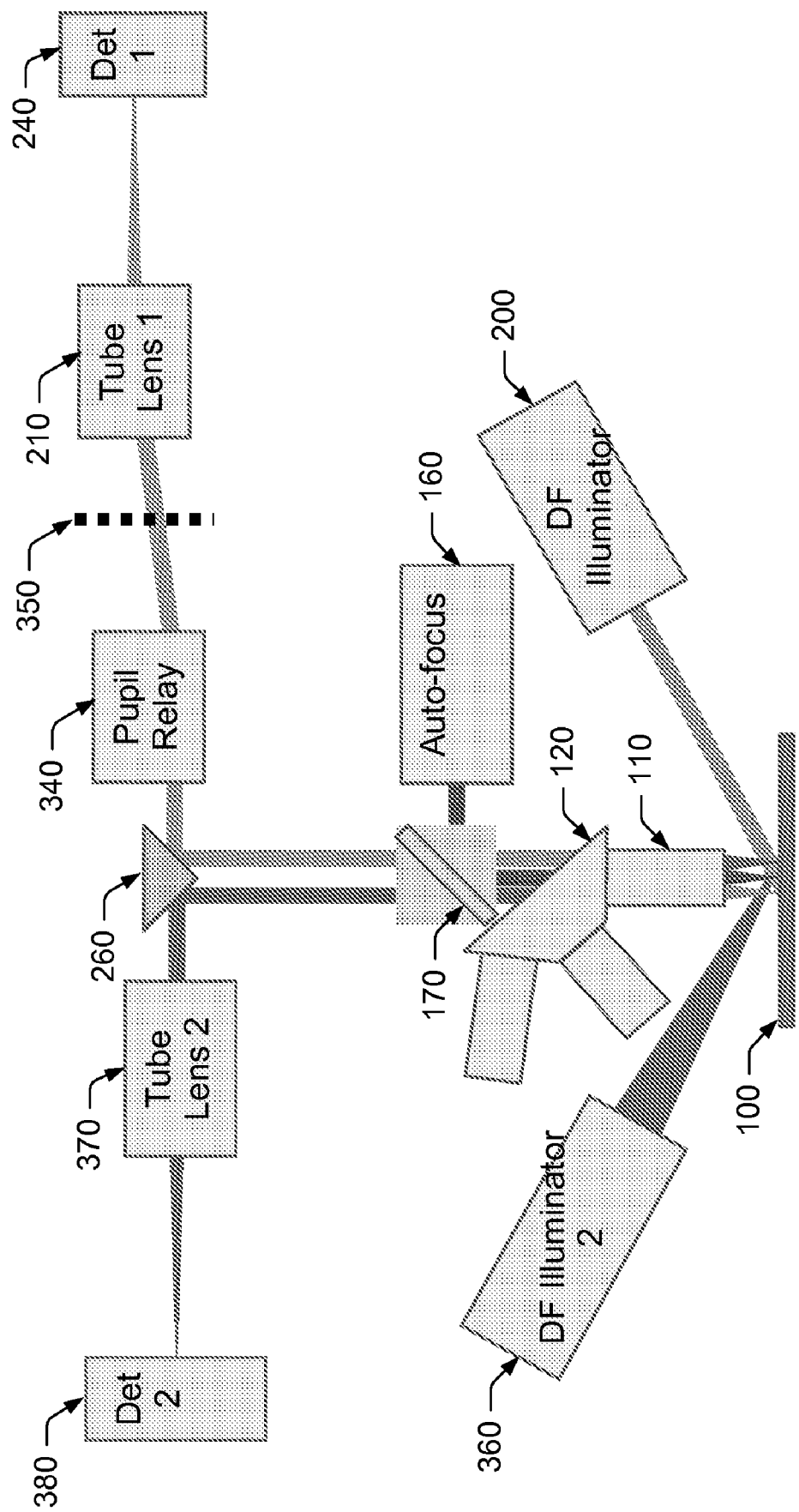
FIG. 6 is a block diagram illustrating one embodiment of a system configured to inspect a specimen with two dark-field channels.

FIG. 6 illustrates another alternative embodiment of the spatial separation method, in which two dark-field channels are used for inspecting different regions of the wafer. Many of the components shown in FIG. 6 are identical to the ones shown in FIG. 5. Components having like reference numerals will not be described further herein. The wafer inspection system shown in FIG. 6 differs from the system of FIG. 5 by eliminating the bright-field illumination subsystem and adding an additional dark-field illuminator 360, dark-field tube lens 370 and dark-field detector 380. Illumination from the dark-field illuminators 200 and 360 is preferably supplied to the surface of the wafer, so that the field of view of one channel crosses over the field of view of the other channel. This is done to reduce cross-talk between the two channels.

In one embodiment, dark-field illuminator 200 includes a laser source and dark-field illuminator 360 includes an LED source. As described below, the first dark-field channel (including the laser source) may be used to inspect regular repeating patterns on the wafer with high sensitivity. The second dark-field channel (including the LED source) may be used to inspect areas of the wafer having somewhat random patterns, such as the logic and periphery regions of a memory chip, with lesser, albeit adequate sensitivity.

For example, light from the first dark-field channel is reflected by prism-shaped mirror 260 to pupil relay 340. Fourier filter 350 is placed at the pupil conjugate to filter out the repeating patterns on the wafer. Once the repeating patterns are filtered out, the array looks like an unpatterned surface to the first dark-field channel. The first dark-field channel provides high sensitivity by using a significantly brighter illumination source (e.g., a laser) and Fourier filtering of the collected light to eliminate the repeating patterns. The filtered image is converged into a real image by dark-field tube lens 210 and detected by dark-field detector 240. On the other side, light from the second dark-field channel is reflected by prism-shaped mirror 260 to dark-field tube lens 370, where it is converged into a real image and subsequently detected by dark-field detector 380. The second dark-field channel provides less sensitivity to small scattering defects, but provides good sensitivity to a wide variety of defect types.

Various embodiments of a system configured for inspecting a specimen have been described herein. Although the embodiments may differ, in one way or another, each of the embodiments described herein includes a dual-channel microscope, two illuminators, each coupled for illuminating a different channel of the dual-channel microscope, two detectors, each coupled to a different channel of the dual-channel microscope for acquiring images of the specimen, and means for separating the channels of the dual-channel microscope, so that the two detectors can acquire the images of the specimen at substantially the same time. The dual-channel microscope may include two bright-field channels, two dark-field channels or one bright-field and one dark-field channel. The channels may be separated spectrally or spatially, as described above in reference to FIGS. 2, 3, 5, and 6.

As mentioned above, the output signals from the two detectors may be supplied to one or more computer systems (not shown) for further processing. For example, the output signals may be supplied to a processor (not shown). The processor may be coupled to the two detectors by a transmission medium (not shown). The transmission medium may include any suitable transmission medium known in the art. In addition, the processor may be coupled to the detector by one or more electronic components (not shown) such as an analog to digital converter. In this manner, the processor may be configured to receive output signals from the detectors.

In some embodiments, the processor may be configured to use the output signals for detecting one or more defects on the specimen. The defects may include any defects of interest on the specimen. In addition, the processor may be configured to perform any other inspection-related functions known in the art (e.g., defect location determination, defect classification, defect mapping, etc.). The processor may take various forms, including a personal computer system, mainframe computer system, workstation, image computer, parallel processor, or any other processing device known in the art. In general, the term "computer system" may be broadly defined to encompass any device having one or more processors, which executes instructions from a memory medium.

Figure 7:
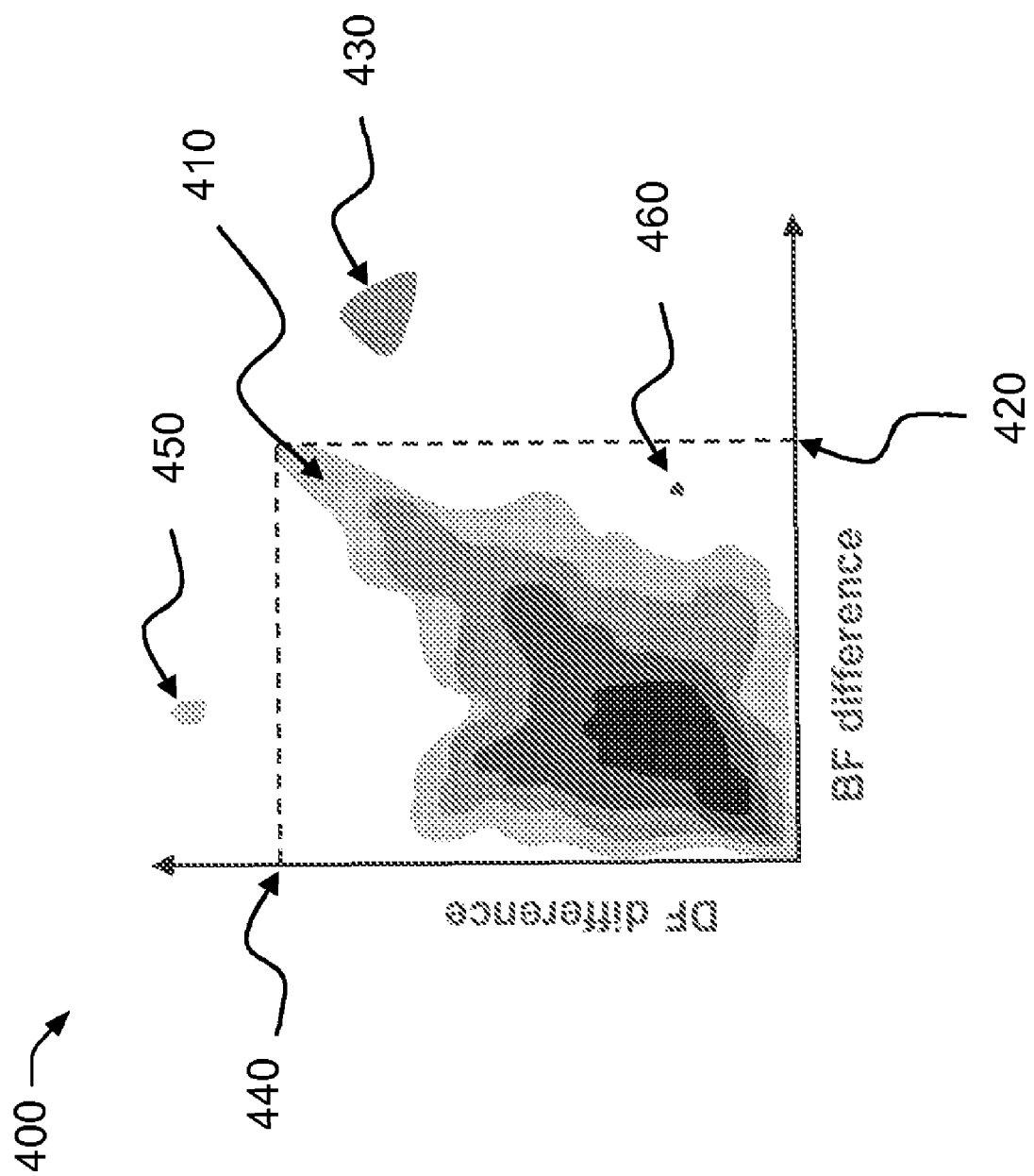
FIG. 7 is an exemplary graph illustrating defects detectable in a one-dimensional and two-dimensional decision space.

The processor may be generally configured to use the output signals and any method and/or algorithm known in the art to detect the defects on the specimen. In one embodiment, the processor may apply a one-dimensional defect detection algorithm to output signals from one of the detectors to detect bright-field defects or dark-field defects. In other embodiments, the process may apply a two-dimensional defect detection algorithm to the combined output signals from both detectors. Applying a two-dimensional algorithm to the combined output signals may increase sensitivity to a wider range of defect types by including defects, which can only be detected in the bright-field difference vs. dark-field difference decision space (i.e., defects below the bright-field and dark-field noise floors, as shown in FIG. 7).

In some embodiments, the inspection systems described herein may be configured as "stand alone tools" or tools that are not physically coupled to a process tool. In other embodiments, the inspection systems described herein may be coupled to a process tool (not shown) by a transmission medium, which may include wired and wireless portions. The process tool may include any process tool known in the art such as a lithography tool, an etch tool, a deposition tool, a polishing tool, a plating tool, a cleaning tool, or an ion implantation tool. The process tool may be configured as a cluster tool or a number of process modules coupled by a common handler. Alternatively, the inspection systems described herein may be integrated into a process tool such as those described above. In some cases, the results of inspection performed by the systems described herein may be used to alter a parameter of a process or a process tool using a feedback control technique, a feedforward control technique and/or an in situ control technique. The parameter of the process or the process tool may be altered manually or automatically.

It will be appreciated to those skilled in the art having the benefit of this disclosure that this invention is believed to provide an improved wafer inspection system with simultaneous bright-field and dark-field inspection. Further modifications and alternative embodiments of various aspects of the invention will be apparent to those skilled in the art in view of this description. In one alternative embodiment, for example, an LED light source may be used within a single channel inspection system. The single channel inspection system may be configured in any manner known in the art. Use of an LED light source would enable a single channel inspection system to reap the benefits mentioned above (e.g., long lifetimes and customization of illumination spectra). It is intended, therefore, that the following claims be interpreted to embrace all such modifications and changes and, accordingly, the specification and drawings are to be regarded in an illustrative rather than a restrictive sense.

What is claimed is:

1. A system for inspecting a specimen, the system comprising:
    a dual-channel microscope;
    two illuminators coupled for illuminating different channels of the dual-channel microscope, such that illumination from the two illuminators is directed to the specimen at the same time;
    two detectors coupled to different channels of the dual-channel microscope for acquiring images of the specimen; and
    means for separating the channels of the dual-channel microscope, so that the two detectors can acquire the images of the specimen at the same time.

2. The system as recited in claim 1, wherein at least one of the illuminators comprises a broadband illumination source.

3. The system as recited in claim 1, wherein at least one of the illuminators comprises a light emitting diode (LED) source.

4. The system as recited in claim 3, wherein the LED source comprises an array of light emitting diodes, each having a coating that enables the diode to produce white light.

5. The system as recited in claim 3, wherein the LED source comprises two or more different colors of light emitting diodes, each configured to produce light in a substantially different spectral range.

6. The system as recited in claim 1, wherein said means include spectrally separating the channels of the dual-channel microscope by configuring the two illuminators so that the illumination is generated or filtered into two substantially non-overlapping spectral ranges.

7. The system as recited in claim 6, wherein the two illuminators are each coupled for providing bright-field illumination to the dual-channel microscope.

8. The system as recited in claim 6, wherein the two illuminators are each coupled for providing dark-field illumination to the dual-channel microscope.

9. The system as recited in claim 6, wherein the two illuminators are separately coupled for providing bright-field and dark-field illumination to the dual-channel microscope.

10. The system as recited in claim 1, further comprising an objective lens coupled for receiving light propagating from the specimen in response to the illumination provided to the specimen by the two illuminators.

11. The system as recited in claim 10, wherein the two detectors each have a field of view over which a respective detector can receive a portion of the light propagating from the specimen, and wherein said means include spatially separating the channels of the dual-channel microscope by positioning the illuminators and the detectors, so that:
    the illumination provided by the two illuminators do not overlap within a field of view of the objective lens; and
    the fields of view of the two detectors do not overlap within the field of view of the objective lens.

12. The system as recited in claim 11, wherein cross-talk between the two channels is reduced by positioning the two illuminators, so that the illumination from one of the illuminators crosses over an illumination path of the other illuminator.

13. The system as recited in claim 11, wherein one of the illuminators is coupled for providing bright-field illumination to the specimen through the objective lens, and wherein the other illuminator is coupled for providing dark-field illumination to the specimen outside of the objective lens.

14. The system as recited in claim 11, wherein the two illuminators are each coupled for providing dark-field illumination to the specimen outside of the objective lens.

15. The system as recited in claim 11, wherein one of the illuminators includes a laser source, and wherein the other illuminator includes an LED source.

16. The system as recited in claim 11, wherein the two illuminators each include an LED source.

17. A system for inspecting a specimen, the system comprising:
   a pair of illumination subsystems coupled for directing a first beam of light and a second beam of light to the specimen at the same time, wherein at least one of the illumination subsystems comprises a light emitting diode (LED) source;
   an objective lens coupled for receiving light propagating from the specimen in response to the first and second beams of light; and
   a pair of detection subsystems, each coupled for generating output signals in response to a respective portion of the light propagating from the specimen, wherein the output signals are generated at the same time.

18. The system as recited in claim 17, wherein the LED source comprises an array of light emitting diodes, each having a coating that enables the diode to produce white light.

19. The system as recited in claim 17, wherein the LED source comprises an array of light emitting diodes including at least two different colors of LEDs.

20. The system as recited in claim 19, wherein the LED source can be configured to produce white light by supplying approximately the same amount of current to each LED in the array.

21. The system as recited in claim 19, wherein the LED source can be customized to produce light in a substantially different spectral range by varying the amount of current supplied to one or more LEDs in the array.

22. The system as recited in claim 17, wherein the pair of illumination subsystems each include a bright-field illuminator.

23. The system as recited in claim 17, wherein the pair of illumination subsystems each include a dark-field illuminator.

24. The system as recited in claim 17, wherein the pair of illumination subsystems include one bright-field illuminator and one dark-field illuminator.

25. The system as recited in claim 17, wherein each detection subsystem has a field of view, which is positioned within a field of view of the objective lens.

26. The system as recited in claim 25, further comprising separation means configured to prevent light propagating from the specimen in response to the first beam of light from interfering with light propagating from the specimen in response to the second beam of light.

27. The system as recited in claim 26, wherein the separation means are provided by configuring the pair of illumination subsystems, such that each generates light in a substantially different, non-overlapping spectral range.

28. The system as recited in claim 26, wherein the separation means are provided by arranging the pair of illumination subsystems and the pair of detection subsystems, so that:
   the first and second beams of light are spatially separated from one another within the field of view of the objective lens; and
   the fields of view of the detection subsystems are spatially separated from one another within the field of view of the objective lens.

29. A method for inspecting a specimen with simultaneous bright-field and dark-field illumination, the method comprising:
   generating bright-field illumination with one light source and dark-field illumination with another light source;
   supplying the bright-field illumination and the dark-field illumination to the specimen at the same time;
   detecting, at the same time, light reflected from the specimen in response to the bright-field illumination, as well as light scattered from the specimen in response to the dark-field illumination.

30. The method as recited in claim 29, wherein the step of generating comprises using a light emitting diode (LED) source to generate the bright-field illumination, the dark-field illumination or both.

* * * * *